(12) United States Patent
Wang et al.

(10) Patent No.: US 7,273,471 B1
(45) Date of Patent: Sep. 25, 2007

(54) CATHETER BALLOON HAVING A POROUS LAYER WITH RIDGES

(75) Inventors: Edwin Wang, Tustin, CA (US); Jon Becker, Danville, CA (US); Florencia Lim, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 547 days.

(21) Appl. No.: 10/746,621

(22) Filed: Dec. 23, 2003

(51) Int. Cl.
*A61M 29/00* (2006.01)
*A61M 31/00* (2006.01)
*A61M 37/00* (2006.01)

(52) U.S. Cl. .................. 604/103.08; 604/103.09; 604/103.11; 604/103.06

(58) Field of Classification Search ............... 604/103.06–103.11, 96.01; 606/194
See application file for complete search history.

(56) References Cited

U.S. PATENT DOCUMENTS

| | | |
|---|---|---|
| 4,651,721 A | 3/1987 | Mikulich et al. |
| 4,796,629 A * | 1/1989 | Grayzel .................. 606/194 |
| 5,112,304 A * | 5/1992 | Barlow et al. ......... 604/103.09 |
| 5,195,970 A | 3/1993 | Gahara |
| 5,196,024 A | 3/1993 | Barath |
| 5,250,070 A | 10/1993 | Parodi |
| 5,320,634 A | 6/1994 | Vigil et al. |
| 5,336,234 A | 8/1994 | Vigil et al. |
| 5,357,978 A | 10/1994 | Turk |
| 5,454,795 A | 10/1995 | Samson |
| 5,456,666 A | 10/1995 | Campbell et al. |
| 5,458,572 A | 10/1995 | Campbell et al. |
| 5,505,702 A | 4/1996 | Arney |
| 5,616,149 A | 4/1997 | Barath |
| 5,628,746 A | 5/1997 | Clayman |
| 5,637,091 A | 6/1997 | Hakky et al. |
| 5,649,941 A | 7/1997 | Lary |
| 5,653,690 A | 8/1997 | Booth et al. |
| 5,746,968 A | 5/1998 | Radisch, Jr. |
| 5,752,934 A | 5/1998 | Campbell et al. |
| 5,797,935 A | 8/1998 | Barath |
| 5,807,326 A | 9/1998 | O'Neill et al. |
| 5,868,704 A | 2/1999 | Campbell et al. |
| 6,110,192 A | 8/2000 | Ravenscroft et al. |
| 6,120,477 A | 9/2000 | Campbell et al. |
| 6,210,392 B1 | 4/2001 | Vigil et al. |
| 6,258,108 B1 | 7/2001 | Lary |
| 6,375,637 B1 | 4/2002 | Campbell et al. |
| 6,428,506 B1 | 8/2002 | Simhambhatla et al. |
| 6,528,150 B2 | 3/2003 | Nazarova et al. |
| 6,540,693 B2 | 4/2003 | Burbank et al. |
| 6,562,062 B2 | 5/2003 | Jenusaitis et al. |
| 6,602,224 B1 | 8/2003 | Simhambhatla |
| 6,695,809 B1 * | 2/2004 | Lee .................. 604/96.01 |
| 6,746,425 B1 * | 6/2004 | Beckham ............. 604/103.09 |

(Continued)

FOREIGN PATENT DOCUMENTS

WO     WO95/05555     2/1995

*Primary Examiner*—Catherine S. Williams
(74) *Attorney, Agent, or Firm*—Fulwider Patton LLP

(57) ABSTRACT

A balloon catheter having a balloon with a porous polymer layer and one or more filamentary members which are on or in the porous polymer layer and which form ridges protruding outwardly from a surface of the balloon in the inflated configuration. In a presently preferred embodiment, the balloon has a wingless noninflated configuration.

22 Claims, 4 Drawing Sheets

U.S. PATENT DOCUMENTS

| | | | |
|---|---|---|---|
| 6,942,680 B2 * | 9/2005 | Grayzel et al. | 606/194 |
| 6,977,103 B2 * | 12/2005 | Chen et al. | 428/35.7 |
| 6,989,025 B2 * | 1/2006 | Burgmeier et al. | 623/1.11 |
| 6,991,617 B2 * | 1/2006 | Hektner et al. | 604/103.01 |
| 2002/0010489 A1 * | 1/2002 | Grayzel et al. | 606/194 |
| 2003/0033001 A1 * | 2/2003 | Igaki | 623/1.11 |
| 2004/0082965 A1 * | 4/2004 | Beckham | 606/192 |
| 2005/0123702 A1 * | 6/2005 | Beckham | 428/36.3 |
| 2006/0085023 A1 * | 4/2006 | Davies et al. | 606/192 |

* cited by examiner

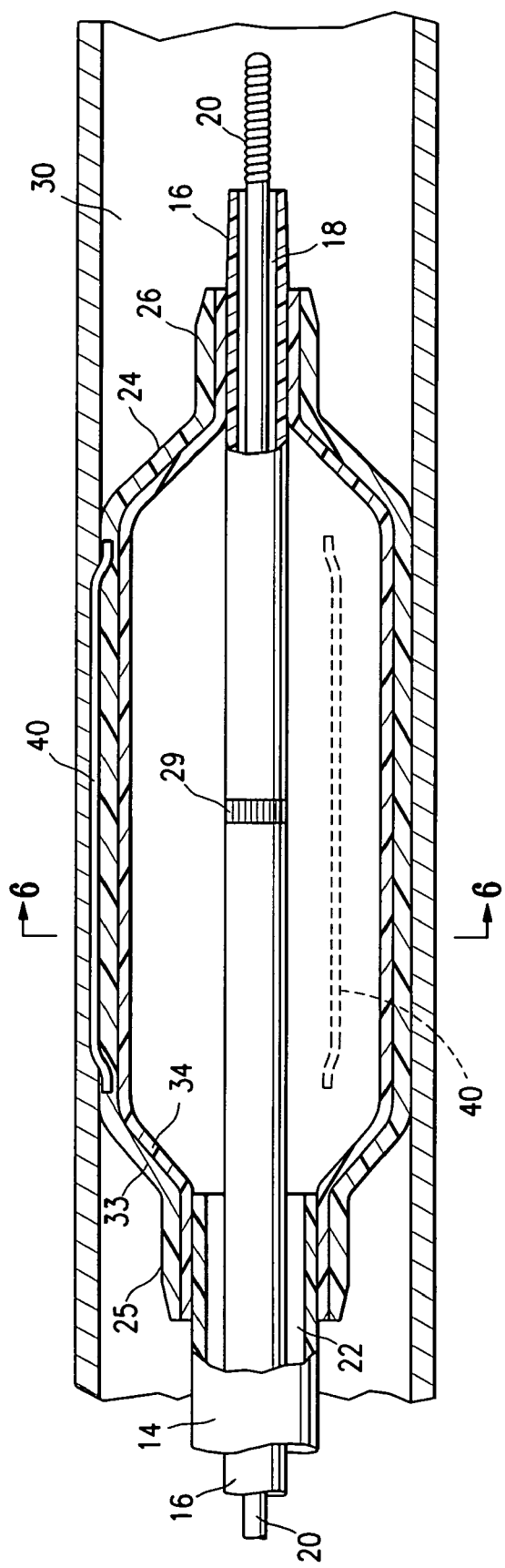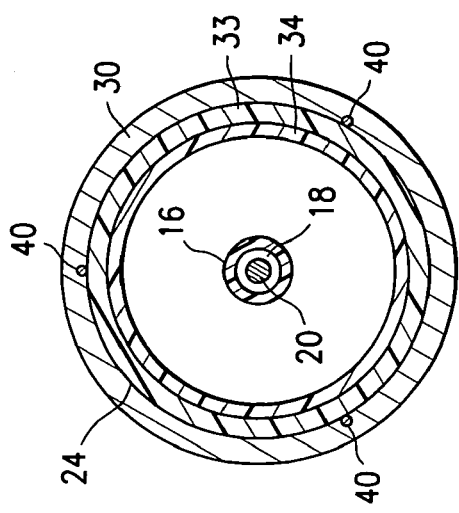
FIG. 5
FIG. 6

CATHETER BALLOON HAVING A POROUS LAYER WITH RIDGES

BACKGROUND OF THE INVENTION

This invention generally relates to catheters, and particularly balloon catheters used in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the lesion is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e., reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. A tubular cover formed of synthetic or natural material may be present on an outer or inner surface of the stent. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. Consequently, a variety of polymeric materials are conventionally used in catheter balloons. Use of polymeric materials such as nylon, polyethylene, and PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which instead readily expand to the working diameter within the patient's body lumen from a generally cylindrical or tubular shape (i.e., essentially no wings) that conforms to the catheter shaft.

An essential step in effectively performing a PTCA procedure is properly positioning the balloon catheter at a desired location within the coronary artery. To facilitate advancement of the catheter within the tortuous vasculature, conventional balloon catheters for angioplasty and stent delivery frequently have a lubricious coating on at least a portion of an outer surface of the catheter. However, one difficulty has been the tendency of the balloon to slip out of position during inflation of the balloon. Accordingly, it would be a significant advance to provide a catheter balloon having improved balloon retention, and without inhibiting movement of the catheter within the vasculature.

SUMMARY OF THE INVENTION

The invention is directed to a balloon catheter having a balloon with a polymeric layer formed of porous polymer and one or more filamentary members which are on or in the porous polymer layer. Preferably, the filamentary members form ridges protruding outwardly from a surface of the balloon in the inflated configuration. In a presently preferred embodiment, the balloon has a wingless noninflated configuration.

In a presently preferred embodiment, a balloon catheter of the invention generally comprises an elongated shaft having a proximal end, a distal end, and an inflation lumen therein, and a balloon on a distal shaft section having an interior in fluid communication with the inflation lumen. The balloon inflates from a wingless noninflated configuration to an inflated configuration with a cylindrical surface section, and has a porous polymer outer layer, and a nonporous polymer inner layer, with the filamentary member(s) on or in the porous polymer outer layer to form ridges protruding outwardly from the balloon along at least the cylindrical surface section of the inflated balloon. The ridges formed by the filamentary members provide an irregular surface which in one embodiment enhances frictional engagement between the balloon and adjacent surfaces such as the wall of a patient's blood vessel as the balloon is inflated into contact with the vessel wall. Although discussed herein typically in terms of a balloon having multiple filamentary members, it should be understood that the balloon can have a single filamentary member.

In one embodiment, the filamentary members are totally or partially embedded within the porous polymeric layer. For example, in an embodiment in which the porous polymeric layer is formed by wrapping porous polymeric tape and heating overlapping sections of the wrapped tape together to form a tube, the filamentary members can be positioned between the overlapping wrapped sections of the porous polymeric material before the wrapped tape is heat fused to form the tube. In one embodiment, the filamentary members are covered with only the outer-most sections of the wrapped porous polymeric tape, which maximizes the effect of the resulting ridges formed by the embedded filamentary members. In an alternative embodiment, the filamentary members are applied to an outer surface of the porous polymeric layer, with the entire length of the filamentary members applied to the outer surface or alternatively with only the filamentary member ends embedded in the porous polymeric layer. The porous polymeric layer of the balloon is typically compressible. As a result, in one embodiment, the filamentary members are pressed down onto the outer surface of the porous polymeric layer so that the porous polymeric material at least partially surrounds the filamentary member. Totally or partially embedding the filamentary members preferably minimizes any increase in profile of the noninflated balloon caused by the filamentary members, while still providing the ridges in the inflated configuration.

In the embodiment in which the balloon is wingless, the noninflated balloon (i.e., in the low profile configuration for advancement within the patient's body lumen prior to being inflated in the body lumen) does not have folded wings. Additionally, in one embodiment, the balloon deflates by elastic recoil to an essentially wingless profile with little or no wings, so that the outer dimensions of the deflated balloon are not substantially greater than the noninflated wingless balloon prior to inflation. In one presently preferred embodiment, the filamentary members are formed of a flexible elastic material such as natural or synthetic silk or a polymer, which prevents or inhibits any tendency of the filamentary members to cause the balloon to form wings as it deflates. However, the filamentary members can be formed of a variety of suitable materials including metallic materials such as stainless steel, nickel titanium (NiTi) alloy, Elgiloy, and cobalt-chromium (Co—Cr), and polymers such as polyurethane, polyamide, silicones, polyethylene, polycarbonate, Chitosan, and MPC (2-methacryloyloxy ethyl phosphorylcholine). In one embodiment, the filamentary members are formed of a radiopaque material to provide visualization of the balloon under fluoroscopy during a medical procedure. For example, in one embodiment the radiopaque filamentary member is formed of gold, iridium, nickel or nickel alloy wires, platinum/iridium and tungsten filled polymer fibers such as nylon and polyurethane, or silk/radiopaque compound composites such as silk coated with barium sulfate (BaS04).

The filamentary member typically has the slender, thread-like structure of a filament such as a metal wire or a silk thread. The filamentary member is preferably a single strand, but it can alternatively be made up of multiple strands twisted together. As the balloon is inflated against a lesion in the body lumen, the filamentary members preferably produce a focalized force on the lesion to thereby create a controlled tear on the luminal surface during dilation. In one embodiment, the diameter of the filamentary member is sufficiently small so that it preferably cuts into the lesion during dilation. However, unlike blade-like cutting structures, the wire-like filamentary member preferably has a curvilinear outer surface (e.g., round or oblong) to minimize unintended damage and injury during advancement of the catheter and inflation of the balloon in the body lumen. In an alternative embodiment, the diameter of a filamentary member with a curvilinear outer surface is sufficiently large to prevent or inhibit it from cutting into the lesion during dilation. However, in an alternative embodiment, the filamentary member has a blade-like cutting structure.

The number of the filamentary members and the nature of the filamentary members (e.g., the disposition on the balloon, dimensions, and material thereof) vary depending on the desired characteristics of the balloon catheter. Preferably, the filamentary members are configured to provide improved dilation of a stenosed region without disadvantageously reducing trackability of the balloon catheter. Thus, in one embodiment, the dimensions and material of the filamentary members are such as to prevent or reduce any disadvantageous increase in stiffness of the distal end of the catheter.

In one embodiment, typically an embodiment in which the balloon has a lubricious outer coating, the balloon has a slip angle which is greater than a slip angle of an identical balloon without the filamentary members. Thus, the filamentary members prevent or inhibit the balloon from slipping out of position as the balloon is inflated in the patient's body lumen. The slip angle is the critical angle at which the coated workpiece will slip out of position. A less lubricious surface has a higher slip angle than a more lubricious surface. A fixture for measuring the slip angle generally comprises a polymeric tube, and specifically a polyvinyl alcohol and dimethyl sulfoxide tube, which simulates a blood vessel, and a pusher with a weight which is on an outer surface of the tube and which can be oriented at different angles relative to the polymeric tube. The balloon is placed in the tube, with the angle at which the pusher contacts the tube simulating the angle of a lesion in a blood vessel, and the angle of the pusher is increased until the balloon slips longitudinally out of position during inflation of the balloon in the tube. Thus, the pusher squeezing on the balloon causes the balloon to slip longitudinally, and the higher the angle at which this slipping first occurs, the less likely the balloon is to slip out of position during inflation of the balloon in a patient's blood vessel. It should be noted that at a relatively high angle of about 20 degrees the pusher begins to pinch the balloon and prevent the balloon from slipping longitudinally in the polymeric tube, so that a slip angle above 20 degrees cannot be measured with the slip angle fixture described above.

A balloon catheter of the invention having the filamentary members on the balloon produces a stress line on a lesion during dilation of the lesion, for improved dilation of the stenosed section of the patient's blood vessel. Additionally, the balloon inflates into contact with, and remains at least partially in contact with the stenosed section of the blood vessel during a dilation due at least in part to the filamentary members. Thus, the balloon catheter provides for improved dilation by preferably reducing the tendency of the balloon to slip proximally or distally from the stenosed section of the blood vessel. Moreover, the balloon catheter is configured to have excellent trackability, and to avoid unintended damage or injury during advancement of the catheter or inflation of the balloon in the body lumen. These and other advantages will become more apparent from the following detailed description and figures.

BRIEF DESCRIPTION OF THE DRAWINGS

FIG. 5 illustrates the balloon catheter of FIG. 1, with the balloon in an inflated configuration.

FIG. 6 illustrates a transverse cross section of the catheter of FIG. 5, taken along line 6-6.

DETAILED DESCRIPTION OF THE PREFERRED EMBODIMENTS

Figure 1:
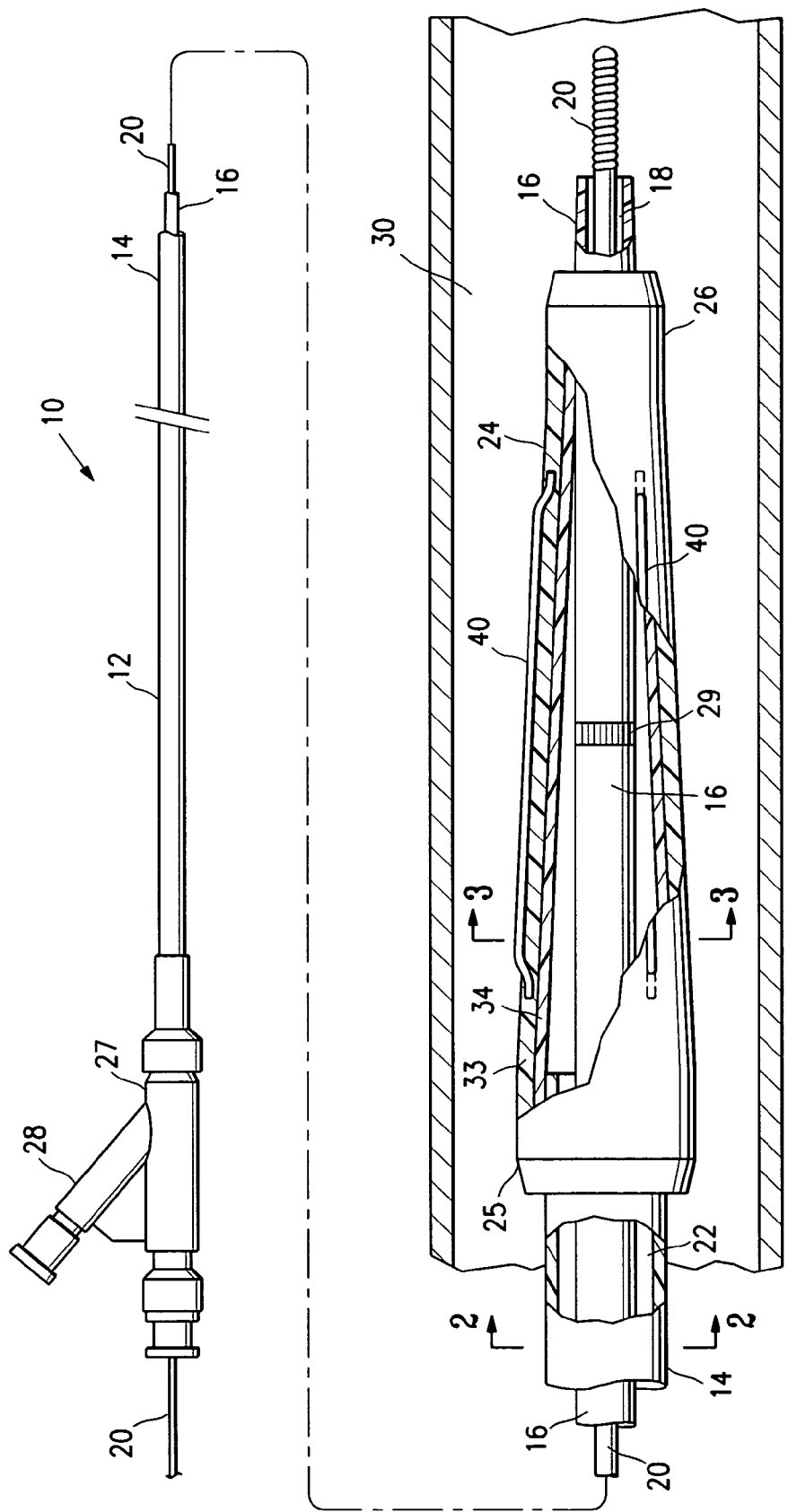
FIG. 1 illustrates an elevational view, partially in longitudinal cross section, of a stent delivery catheter embodying features of the invention.
Figure 2:
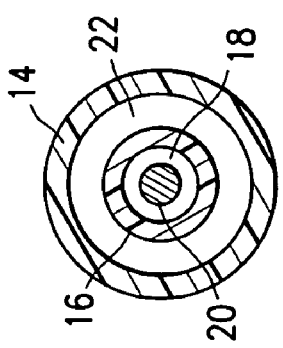

FIG. 1 illustrates an over-the-wire type balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2-2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 27 at the proximal end of catheter shaft 12 is configured to provide access to guidewire lumen 18, and to direct inflation fluid through arm 28 into inflation lumen 22. Radiopaque marker band 29 on the inner tubular member 16 indicates the position of the balloon.

The balloon 24 is illustrated in FIG. 1 in a noninflated configuration. In the embodiment of FIG. 1, balloon 24 has a wingless noninflated configuration. The distal end of catheter 10 may be advanced to a desired region of the patient's body lumen 30 in a conventional manner, the balloon 24 inflated by introducing inflation fluid into the balloon interior. FIGS. 5 and 6 illustrate the balloon in an inflated configuration. The inflated balloon can be deflated to a deflated configuration by withdrawing the inflation fluid from the balloon interior, and the catheter repositioned removed from the body lumen 30. In one embodiment, the balloon 24 deflates to an essentially wingless profile with little or no wings, so that the outer dimensions of the deflated balloon are not substantially larger than the noninflated wingless balloon prior to inflation.

In the embodiment of FIG. 1, balloon 24 has an outer layer 33 and an inner layer 34 extending from the proximal skirt section 25 to the distal skirt section 26. The inner surface of the outer layer 33 is preferably bonded to the inner layer 34, as for example by fusion bonding and/or adhesive bonding, and the balloon 24 is bonded to the shaft 12, preferably by fusion and/or adhesive bonding.

Balloon outer layer 33 preferably comprises a porous polymeric material, such as expanded polytetrafluoroethylene (ePTFE), an ultra high molecular weight polyolefin including ultra high molecular weight polyethylene, porous polyolefins including polyethylene and polypropylene, or porous polyurethane. In one embodiment, the porous material has a node and fibril microstructure. For example, ePTFE and ultra high molecular weight polyethylene (also referred to as "expanded ultra high molecular weight polyethylene") typically have a node and fibril microstructure, and are not melt extrudable. The node and fibril microstructure, when present, is produced in the porous material using conventional methods. Although discussed below primarily in terms of the embodiment in which the porous outer layer 33 is ePTFE, it should be understood that other materials can be used to form outer layer 33. The ePTFE layer 33 is preferably formed according to conventional methods, in which a sheet of ePTFE polymeric material is wrapped with overlapping or abutting edges to form a tubular body and then heated to fuse the wrapped material together. The ePTFE sheet is typically wrapped to form one or more layers, and preferably about two to about five layers, of wrapped material which are heated to fuse the layers together. The sheet of polymeric material preferably has the desired microstructure (e.g., porous and/or node and fibril) before being wrapped on the mandrel. The resulting tube of ePTFE polymeric material is typically further processed by being stretched, sintered, compacted, and sintered again, to provide the desired properties such as the desired dimension, and dimensional stability (e.g., to minimize changes in length occurring during inflation of the balloon). The completed ePTFE layer 33 is then bonded to or otherwise combined with elastomeric liner 34 either before or after layer 34 is bonded to the shaft.

The inner layer 34 is formed of a polymeric material preferably different from the polymeric material of the outer layer 33. Inner layer 34 limits or prevents inflation fluid within the balloon interior from leaking through the microporous ePTFE, to thereby allow for inflation of the balloon 24. The inner layer 34 is preferably formed of an elastomeric material to facilitate deflation of the balloon 24 to a low profile deflated configuration, including polyurethanes, silicone rubbers, polyamide block copolymers, dienes, and the like. Inner layer 34 may consist of a separate layer which neither fills the pores nor disturbs the node and fibril structure of the ePTFE layer 33, or it may at least partially fill the pores of the ePTFE layer 33. Similarly, in one embodiment elastomeric polymer applied as a solution to the ePTFE layer at least partially fills the pores of the porous polymeric ePTFE. Thus, the terminology "porous polymer" as used herein should be understood to refer to the porous structure of the ePTFE polymer whether or not the pores are fully or partially filled with an elastomeric polymer to form the balloon layer 33.

In a presently preferred embodiment, the ePTFE outer layer 33 has a hydrophilic coating (not shown) thereon to facilitate advancing the catheter through the patient's body lumen by reducing the coefficient of friction of the balloon 24.

The balloon 24 has filamentary members 40. In the embodiment of FIG. 1, the filamentary members 40 extend longitudinally along the balloon partially on an outer surface of the outer layer 33. However, the filamentary members can be disposed on the balloon in a variety of configurations. For example, in an alternative embodiment (not shown), a filamentary member 40 extends circumferentially around the circumference of the balloon.

Figure 3:
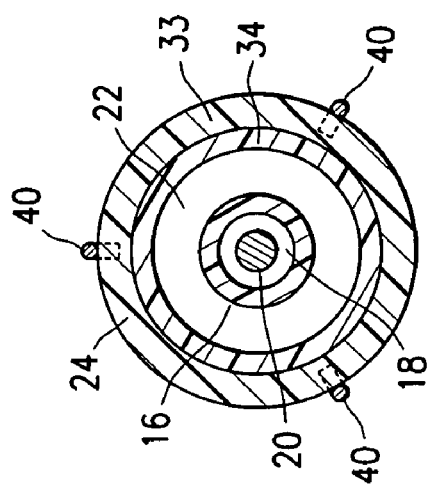
FIGS. 2 and 3 illustrate transverse cross sections of the catheter of FIG. 1, taken along lines 2-2 and 3-3, respectively.

As best illustrated in FIG. 3, three filamentary members are on the balloon 24, and are spaced equidistantly apart around the circumference of the balloon. However, a larger or smaller number of filamentary members 40 can alternatively be used. The number of filamentary members 40 typically ranges from about 1 to about 8, more preferably about 1 to about 5, depending on factors such as the size of the balloon, the degree of lubricity of the balloon outer surface and deliverability of the system.

Figure 4:
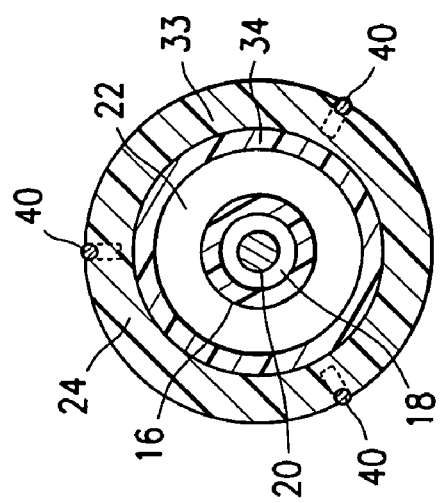
FIG. 4 illustrates a transverse cross section of an alternative embodiment in which the filamentary members are pressed down onto the outer surface of the porous polymeric layer with the porous polymeric material partially surrounding the filamentary members.

As best illustrated in FIG. 3, the filamentary members 40 are positioned on the outer surface of the noninflated balloon 24 with the inner 10% to about 30% of the periphery of the filamentary member in contact with or surrounded by the polymeric material of the porous polymeric outer layer 33 of the balloon 24. In an alternative embodiment illustrated in FIG. 4, the filamentary members 40 are pressed down onto the porous polymeric outer layer 33 to a greater degree, so that about 40% to about 60%, more specifically about 50% of the periphery of the filamentary member 40 is in contact with/surrounded by the polymeric material of the porous polymeric outer layer 33. For example, during or after lamination of the layers 33 and 34 of the balloon 24 to one another, the layers 33, 34 can be radially pressed together, as for example in a balloon press, which, with the filamentary members 40 in place on the outer layer 33, presses the filamentary members 40 down onto the porous outer layer 33. As a result, the filamentary members are fully or partially enveloped by the porous polymeric material of layer 33. The filamentary members can be secured to the catheter before or after the layers 33, 34 are laminated together, but are typically secured to the catheter before the layers are laminated together.

In the embodiment of FIG. 1, the filamentary members are solid-walled with a round transverse cross section. However, a variety of suitable cross sectional shapes can be used including oval, triangular, and crescent shaped. In the illustrated embodiment, the filamentary members have a wall thickness less than the wall thickness of the noninflated porous polymeric layer 33, with the filamentary members having a solid-walled wall thickness which is about 10% to about 80%, more specifically about 20% to about 50%, less than a wall thickness of the porous polymeric layer of the balloon. Typically, the outer diameter of the filamentary members is about 0.02 to about 0.06 mm.

FIGS. 5 and 6 illustrate the distal end of the balloon catheter of FIG. 1, with the balloon 24 inflated to the inflated configuration against the wall of the body lumen 30. The balloon in the inflated configuration has an inflated proximal tapered section, an inflated distal tapered section, and an inflated working length section which is between the proximal and distal tapered sections and which forms a cylindrical surface section of the inflated balloon. The filamentary members 40 extend above the outer surface of the inflated balloon 24 to form protruding ridges in contact with the wall defining the patient's body lumen 30. In the embodiment in which the filamentary members 40 were pressed down onto the outer layer 33 of the noninflated balloon 24 to fully or partially envelope the filamentary members, inflation of the balloon 24 typically causes the filamentary members 40 to be pushed outside the enveloping surface of the outer layer 33 to extend primarily above the outer surface of the outer layer 33 with less than about 20% to about 50% of the periphery of the filamentary members in contact with/ surrounded by the polymeric material of the outer layer 33 in the inflated configuration.

In the illustrated embodiment, the filamentary members extend along the entire cylindrical working length of the balloon between the proximal and distal inflated tapered sections of the balloon. In alternative embodiments (not shown), the filamentary members are shorter than the illustrated embodiment, or alternatively are longer so that the proximal and/or distal ends of the filamentary members are located at the tapered sections of the balloon or at the balloon skirt sections 25, 26. The filamentary members 40 are secured to the balloon 24 along the entire length of the filamentary members 40 or along less than the entire length at one or more locations. For example, in one embodiment, the filamentary members 40 are secured to the balloon only at the ends of the filamentary members, with a nonsecured section between the secured end sections. The filamentary members 40 are typically attached to the balloon 24 by fusion or adhesive bonding depending on the material used to form the filamentary members 40. For example, filamentary members formed of a metallic material or silk are typically secured using an adhesive. Alternatively, filamentary members formed of a polymer can be secured to the balloon by heat fusion bonding.

In the embodiment of FIG. 1, the proximal end and the distal end of each filamentary member 40 are embedded in the porous polymer layer 33 of the balloon 24, with a central section of the filamentary members extending along the outer surface of the layer 33 (i.e., not embedded). In one embodiment, the central section of the filamentary members 40 between the embedded ends is not secured to the balloon outer layer 33, although in an alternative embodiment all or only a portion of the length of the central section is secured to the balloon outer layer 33. Although the embedded ends of the filamentary members 40 are in the central working length section of the balloon in the illustrated embodiment, in an alternative embodiment (not shown), the embedded ends are in the tapered sections of the balloon at either end of the working length section.

Figure 7:
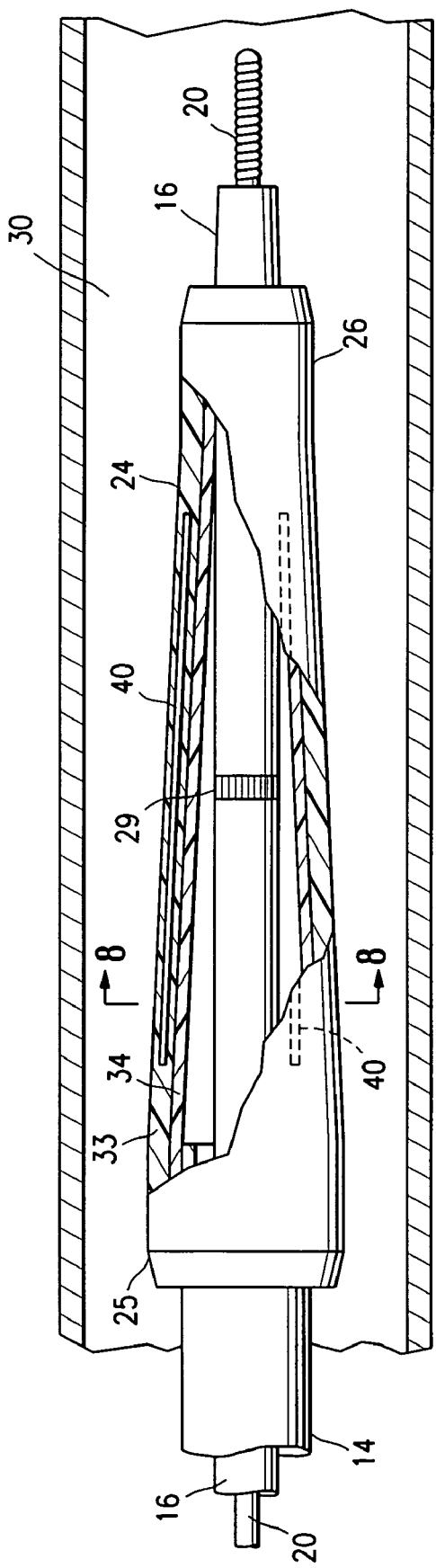
FIG. 7 illustrates a distal end section of a balloon catheter embodying features of an alternative embodiment of the invention, having filamentary members embedded in the outer layer of the balloon.
Figure 8:
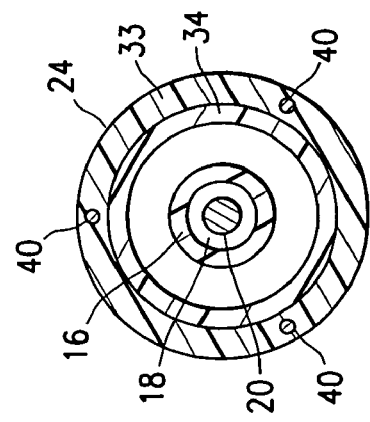
FIG. 8 illustrates a transverse cross section of the catheter of FIG. 7, taken along line 8-8.

FIGS. 7 and 8 illustrate an alternative embodiment of balloon catheter 10, having the filamentary members 40 fully embedded within the outer layer 33 of the noninflated balloon 24. In one embodiment, the embedded filamentary members 40 are preferably closer to the outer surface than to the inner surface of the layer 33, so that the filamentary members 40 form the ridges protruding outwardly from the cylindrical surface section of the balloon 24 in the inflated configuration. In one embodiment, the filamentary members are spaced a sufficiently small distance beneath the outer surface of the layer 33 so that upon inflation of the balloon the filamentary members are forced through the layer 33 to the outer surface of the layer 33 (i.e., the filamentary members 40 tear through the polymeric material of layer 33 as the balloon inflates). As a result, the balloon 24 has low profile, embedded filamentary members in the noninflated configuration which facilitates advancing the noninflated balloon 24 in the body lumen 30, and the balloon has exposed filamentary members protruding from the outer surface of the balloon in the inflated configuration.

Figure 9:
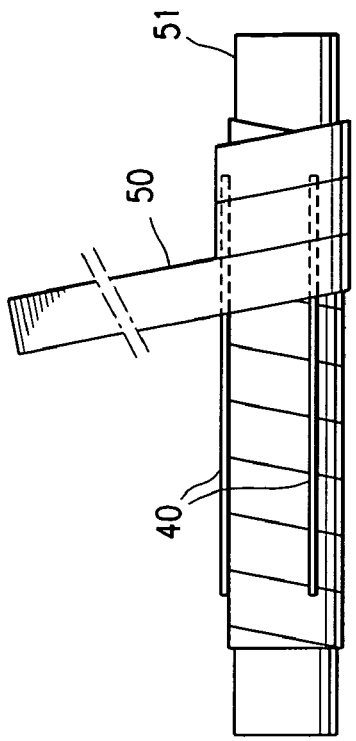
FIG. 9 illustrates a method of forming the balloon illustrated in FIG. 7.

FIG. 9 illustrates a method of forming the balloon illustrated in FIG. 7, in which tape 50 of the porous polymeric material is wrapped on a mandrel 51. Filamentary members 40 are positioned on one or more layers of wrapped tape 50, and the tape is further wrapped to cover the filamentary members with one or more additional layers of wrapped tape. The wrapped assembly is then heated to fuse the adjacent wrapped sections of tape 50 together to form a tube. The porous polymeric layer 33 having the filamentary members 40 on the outer surface thereof in the noninflated configuration is typically formed by a similar process, but with the filamentary members applied to the outer surface of the tube after the wrapped layers are heat fused together. In either case, the porous polymeric layer 33 is typically processed by being longitudinally and/or radially compressed before or after being combined with the filamentary members 40. In a presently preferred embodiment, the porous polymeric layer is compressed before being combined with filamentary members 40. The compression typically reduces but does not destroy the porosity of the porous polymeric material. Thus, in one embodiment, although the porosity of the porous polymeric layer 33 in the noninflated configuration is reduced to low levels by compression, the inflation of the balloon 24 reverses the compression and increases the porosity in the inflated configuration.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), more specifically about 0.037 inch (0.094 cm), and a wall thickness of about 0.002 to about 0.008 inch (0.0051 to 0.02 cm), more specifically about 0.003 to 0.005 inch (0.0076 to 0.013 cm). The inner tubular member 16 typically has an inner diameter of about 0.01 to about 0.018 inch (0.025 to 0.046 cm), more specifically about 0.015 to about 0.016 inch (0.038 to 0.04 cm), and a wall thickness of 0.002 to 0.005 inch (0.005 to 0.013 cm). The overall working length of the catheter 10 may range from about 100 to about 150 cm, and is typically about 143 cm. The balloon 24 typically has a length of about 5 to about 60 mm, more specifically about 8 to about 30 mm, and an inflated working diameter of about 2 to about 10 mm, more specifically about 2 to about 5 mm.

Although the illustrated embodiments include radiopaque marker 29 on the section of the shaft 12 in the balloon 24, it should be understood that the radiopaque marker 29 is omitted in one embodiment in which the filamentary members have at least a section which is radiopaque. Additionally, although the shaft 12 is illustrated as having an inner and outer tubular member, a variety of suitable shaft configurations may be used including a dual lumen extruded shaft having a side-by-side lumens extruded in at least a section thereof. Similarly, although the embodiment illustrated is an over-the-wire catheter, the catheter may comprise other types of intravascular catheters, such as a rapid exchange balloon catheter. Rapid exchange catheters generally comprise a distal guidewire port in a distal end of the catheter, a proximal guidewire port in a distal shaft section and typically spaced a substantial distance from the proximal end of the catheter, and a short guidewire lumen extending between the proximal and distal guidewire ports in the distal section of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. A balloon catheter, comprising:
   a) an elongated shaft having a proximal end, a distal end, and an inflation lumen therein; and
   b) a balloon on a distal shaft section, having an interior in fluid communication with the inflation lumen, which inflates from a wingless noninflated configuration to an inflated configuration which has a cylindrical surface section, and having a non-melt extruded porous polymer outer layer, and a nonporous polymer inner layer, and one or more filamentary members on or in the porous polymer outer layer, the filamentary members emerging from the porous polymer outer layer and forming ridges protruding outwardly from the balloon along at least the cylindrical surface section in the inflated configuration wherein the filamentary members and the porous polymer outer layer are configured to be removed together from the patient after use.

2. The balloon catheter of claim 1 wherein the balloon in the inflated configuration has a proximal skirt section secured to the shaft, a distal skirt section secured to the shaft, an inflated proximal tapered section, an inflated distal tapered section, and an inflated working length section which is between the proximal and distal tapered sections and which forms the cylindrical surface section of the inflated balloon.

3. The balloon catheter of claim 1 wherein the filamentary members extend only along the working length section of the balloon.

4. The balloon catheter of claim 1 wherein the filamentary members extend along the working length section and at least one of the proximal and distal tapered sections of the balloon.

5. The balloon catheter of claim 1 wherein the balloon deflates from the inflated configuration by elastic recoil to an essentially wingless deflated configuration with outer dimensions which are not substantially larger than the wingless noninflated configuration.

6. The balloon catheter of claim 5 wherein the filamentary members comprise silk.

7. The balloon catheter of claim 1 wherein the filamentary members comprise a material selected from the group consisting of silk, a metal, and a polymer.

8. The balloon catheter of claim 1 wherein the filamentary members have a circular or oblong transverse cross sectional shape forming a curvilinear outer surface.

9. The balloon catheter of claim 1 wherein the filamentary members have an outer diameter of about 0.02 to about 0.06 mm.

10. The balloon catheter of claim 1 wherein the filamentary members have a solid-walled wall thickness which is about 10% to about 50% less than a wall thickness of the porous polymer layer of the balloon.

11. The balloon catheter of claim 1 wherein the filamentary members are on an outer surface of the porous polymer outer layer of the balloon.

12. The balloon catheter of claim 11 wherein the filamentary members have at least a section secured to an outer surface of the balloon.

13. The balloon catheter of claim 11 wherein the filamentary members have a proximal and a distal end section fixedly secured to the balloon or the shaft and an unsecured section which is between the proximal and distal end sections and which is not secured to the catheter.

14. The balloon catheter of claim 1 wherein the filamentary members are embedded in the porous polymer outer layer.

15. The balloon catheter of claim 14 wherein the filamentary members are beneath at least an outermost section of multiple overlapping sections of porous polymeric material forming the porous polymer outer layer, and the filamentary members are closer to an outer surface than an inner surface of the porous polymer outer layer.

16. The balloon catheter of claim 15 wherein the filamentary members are beneath at least the outermost section of the multiple overlapping sections of porous polymeric material in the noninflated configuration, and are releasable from beneath the outermost section of the porous polymeric material, so that the filamentary members are on an outer surface of the porous polymer outer layer in the inflated configuration.

17. The balloon catheter of claim 1 wherein the filamentary members extend longitudinally along the balloon and are spaced apart around the circumference of the balloon.

18. The balloon catheter of claim 1 wherein the filamentary member extends circumferentially around the circumference of the balloon.

19. The balloon catheter of claim 1 wherein the filamentary members extend only longitudinally and not circumferentially along the balloon.

20. The balloon catheter of claim 17 wherein the balloon has 1 to 8 filamentary members only.

21. A balloon catheter, comprising:
a) an elongated shaft having a proximal end, a distal end, and an inflation lumen therein; and
b) a balloon on a distal shaft section, having an interior in fluid communication with the inflation lumen, which inflates from a wingless noninflated configuration to an inflated configuration which has a cylindrical surface section, and having a porous polymer outer layer, and a nonporous polymer inner layer, and one or more filamentary members on or in the porous polymer outer layer, the filamentary members forming ridges protruding outwardly from the balloon along at least the cylindrical surface section in the inflated configuration, wherein the filamentary members are contained beneath at least an outermost section of the porous polymeric material in the noninflated configuration, and are releasable from beneath the outermost section of the porous polymeric material, so that the filamentary members are on an outer surface of the porous polymer outer layer in the inflated configuration.

22. A balloon catheter, comprising:
a) an elongated shaft having a proximal end, a distal end, and an inflation lumen therein; and
b) a balloon on a distal shaft section, having an interior in fluid communication with the inflation lumen, which inflates from a wingless noninflated configuration to an inflated configuration which has a cylindrical surface section, and having a porous polymer outer layer, and a nonporous polymer inner layer, and one or more filamentary members on the porous polymer outer layer, the filamentary members forming ridges protruding outwardly from the balloon along at least the cylindrical surface section in the inflated configuration, wherein the filamentary members are fully or partially enveloped by the porous polymer outer layer in the noninflated configuration by an amount which decreases as the balloon inflates to the inflated configuration, such that less but at least some of a periphery of the filamentary members is in contact with the porous polymer outer layer in the inflated configuration than in the noninflated configuration.

* * * * *